| United States Patent [19] | [11] Patent Number: 4,913,724 |
|---|---|
| Poss | [45] Date of Patent: Apr. 3, 1990 |

[54] HERBICIDAL TETRAZOLINONES

[75] Inventor: Kathleen M. Poss, Lawrenceville, N.J.

[73] Assignee: FMC Corporation, Philadelphia, Pa.

[21] Appl. No.: 338,029

[22] Filed: Apr. 14, 1989

[51] Int. Cl.$^4$ .................. C07D 257/04; A01N 43/64
[52] U.S. Cl. .......................................... 71/92; 548/251
[58] Field of Search ............................. 548/251; 71/92

[56] References Cited

U.S. PATENT DOCUMENTS

| 4,318,731 | 3/1982 | Kajioka et al. | 71/92 |
|---|---|---|---|
| 4,439,229 | 3/1984 | Swithenbank | 71/96 |

FOREIGN PATENT DOCUMENTS

| 0068822 | 1/1983 | European Pat. Off. |
| 3603789 | 8/1987 | Fed. Rep. of Germany |
| 58-225070 | 6/1982 | Japan |

OTHER PUBLICATIONS

PTC International Application No. WO 87/07602, Dec. 17, 1987.
PTC International Application No. 86/04481, Aug. 14, 1986.
PTC International Application No. WO 85/01939, May 9, 1985.

Primary Examiner—David B. Springer
Attorney, Agent, or Firm—Beverly K. Johnson; Robert M. Kennedy; H. Robinson Ertelt

[57] ABSTRACT

A herbicidal compound which is a Q-substituted 1-phenyl-4-substituted-1,4-dihydro-5H-tetrazol-5-one in which the Q-substituent is bonded to the ring-carbon atom at the 5-position of the phenyl group and in which:

Q is —CH($R^2$)C($R^3$) ($R^4$)Q' or —C($R^2$)=C($R^4$)Q';

$R^2$ and $R^3$ are each, independently, hydrogen, alkyl, or halogen;

$R^4$ is hydrogen or lower alkyl;

Q' is COOH, COOZ, COO$R^5$, CON($R^6$) ($R^7$), CN, CHO or C(O)$R^5$;

Z is a salt-forming cation;

$R^5$ is alkyl, cycloalkyl or aralkyl;

each of $R^6$ and $R^7$ is, independently, hydrogen, alkyl, cycloalkyl, alkenyl, alkynyl, alkoxy, phenyl, benzyl or SO$_2R^8$, or is one of said radicals substituted by halogen, alkyl or cyano, $R^8$ being the same as $R^6$ other than hydrogen or SO$_2R^8$; said compound being one whose 5-Methoxy Analog and 5-Propargyloxy Analog are herbicides.

36 Claims, No Drawings

HERBICIDAL TETRAZOLINONES

This invention relates to herbicidal 1-aryl-4-substituted-1,4-dihydro-5H-tetrazol-5-ones (tetrazolinones).

The herbicidal activity of certain 1-aryl-4-substituted-1,4-dihydro-5H-tetrazol-5-ones has been described in the patent literature, as in International patent publications WO 86/01939 and WO 87/03873. Particularly useful are compounds in which the aryl group is 2,4,5-substituted.

The compounds of this invention are herbicidal 1-aryl-4-substituted-1.4-dihydro-5H-tetrazol-5-ones such as those of the prior art mentioned above in which, however, the carbon atom at the 5-position of the benzene ring carries a substituent (Q) as described below:

Q is a group of the formula:
—$CH(R^2)C(R^3)(R^4)Q'$ or —$C(R^2)=C(R^4)Q'$ in which Q' is a carboxylic acid group (i.e. COOH) or a salt, ester, amide, or nitrile of such carboxylic acid group. Thus Q' may be:
$CO_2H$,
$CO_2Z$,
$CO_2R^5$,
$CON(R^6)(R^7)$, or
CN.

In another aspect of this invention Q' may be an aldehydic or ketonic group, e.g. —CHO or —$COR^5$.

Z may be a salt-forming cation, such as one which forms a base addition salt with a carboxylic acid, e.g., a sodium, potassium, calcium, ammonium, magnesium, or mono-, di- or tri($C_{1-4}$ alkyl)ammonium or sulfonium or sulfoxonium ion. $R^5$ may be alkyl, cycloalkyl (e.g., of 3 to 6 carbon atoms such as cyclopropyl or cyclopentyl), or aralkyl such as benzyl or substituted benzyl (e.g., chlorobenzyl, alkylbenzyl, or haloalkylbenzyl, such as 4-chlorobenzyl or 4-trifluoromethylbenzyl). $R^6$ and $R^7$ may each, independently, be hydrogen, hydroxy, alkyl, cycloalkyl, alkenyl, alkynyl (e.g., propynyl), alkoxy, phenyl, benzyl, or $SO_2R^8$ (in which $R^8$ is the same as $R^6$ other than hydrogen or $SO_2R^8$), or any of the foregoing carrying additional substituents; such additional substituents may be halogen (e.g., in haloalkyl such as chloroethyl, halophenyl such as chlorophenyl, halobenzyl such as chlorobenzyl), alkyl, or cyano.

In the foregoing formula for Q, $R^2$ and $R^3$ may each, independently, be hydrogen, alkyl (e.g. lower alkyl such as methyl) or halogen (such as chlorine, bromine, or fluorine), while $R^4$ may be hydrogen or lower alkyl.

The other substituents on the herbicidal 1-aryltetrazolinones of this invention may, for instance, be any of those present in the herbicidal aryl tetrazolinones of the prior art mentioned above. For instance those other substituents are so chosen that the 5-Methoxy and 5-Propargyloxy Analogs of the compounds of this invention are herbicides; the 5-Methoxy Analog of a compound of this invention has a formula which is identical with that of the compound of this invention in all respects except that the ring-carbon atom at the 5-position of the benzene ring carries a methoxy substituent instead of a substituent Q as defined above. Similarly, the 5-Propargyloxy Analog is otherwise identical except that the carbon at the 5-position of its benzene ring carries a propargyloxy substituent instead of a substituent Q as defined above. Thus the 5-Methoxy Analog of compounds 1-4 of Table 1 below is 1-(2-fluoro-4-chloro-5-methoxyphenyl) -1,4-dihydro-4-(3-fluoropropyl)-5H-tetrazol-5-one and the Propargyloxy Analog of compounds 1-4 is 1(2-fluoro-4-chloro-5-propargyloxyphenyl) -1,4-dihydro-4-(3-fluoropropyl)-5H-tetrazol-one.

The compounds of this invention preferably have 5-Methoxy Analogs and 5-Propargyloxy Analogs of marked herbicidal properties. For instance, said Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species; velvetleaf (*Abutilon theophrasti*), green foxtail (*Setaria viridis*); Modes: preemergent, postemergent. Testing for such herbicidal activity may be carried out in the manner described below under the heading "Herbicidal Activity".

Representative compounds of this invention are listed in Table 1 below.

One may describe many of the compounds of this invention by the formulas

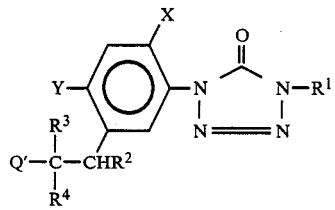

Formula I

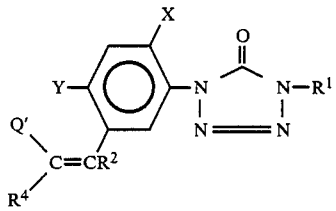

Formula II in which Q', $R^2$, $R^3$ and $R^4$ have the meanings set forth above and the substituent $R^1$ on the tetrazolinone ring may be any of those known in the prior art discussed above. For instance, $R^1$ may be alkyl (preferably of 1 to 6 carbon atoms), haloalkyl (preferably of 1 to 5 carbon atoms), alkoxyalkyl (preferably of 2 to 6 carbon atoms), alkylthioalkyl (preferably of 2 to 6 carbon atoms), cyanoalkyl (preferably of 1 to 5 alkyl carbon atoms), haloalkoxyalkyl (preferably of 2 to 6 carbon atoms), trifluoromethylthio, alkenyl (preferably of 2 to 5 carbon atoms), or haloalkenyl (preferably of 2 to 5 carbon atoms).

In a sub-genus for $R^1$, that group may be alkyl of 1 to 6 carbon atoms such as n-$C_3H_7$; a fluoroalkyl radical of 1 to 5 carbon atoms and one or more fluorine atoms, especially a fluoropropyl radical such as 3-fluoropropyl; alkoxyalkyl or alkylthioalkyl of 2 to 4 carbon atoms such as methoxymethyl or its thio analog; cyanoalkyl of 1 to 3 alkyl carbon atoms such as cyanomethyl; fluoroalkoxyalkyl of 2 to 4 carbon atoms, for example, 2-(difluoromethoxy)ethyl; alkenyl of 3 to 5 carbon atoms such as 2-propenyl; or haloalkenyl of 3 to 5 carbon atoms, for example, a fluoroalkenyl such as 3-fluoro-2-propenyl. In a preferred embodiment $R^1$ is n-$C_3H_7$ or a fluoropropyl radical such as 3-fluoropropyl. Typical $R^1$ groups include —$CH_3$, —$CH_2CH_3$, —$(CH_2)_2CH_3$, —$CH(CH_3)_2$, —$(CH_2)_3CH_3$, —$CH_2CH(CH_3)_2$, —$CH(CH_3)CH_2CH_3$, —$CHF_2$, —$CH_2CH_2Cl$, —$CF_2CF_2CF_3$, —$CF_2CHF_2$, —$CH_2CH_2F$, —$(CH_2)_2CH_2F$, —$(CH_2)_2CH_2Br$, —$(CH_2)_2CHF_2$, —CH$_2$CHFCH$_3$, —CH$_2$CF$_2$CH$_3$, —CH$_2$OCH$_3$, —CH$_2$OCH$_2$CH$_3$, —CH$_2$SCH$_3$, CH$_2$CN, —CH$_2$CH$_2$OCHF$_2$, —SCF$_3$, —CH=CH$_2$, —CH$_2$CH=CH$_2$, and —CH$_2$CH=CHF.

X may be hydrogen; halogen such as chlorine, bromine, or fluorine (preferably fluorine or chlorine); alkyl such as lower alkyl (e.g. methyl); haloalkyl such as halo lower alkyl (e.g., CF$_3$, CH$_2$F or CHF$_2$); alkoxy such as lower alkoxy (e.g., methoxy); or nitro; and Y may be hydrogen; halogen such as chlorine, bromine, or fluorine (preferably bromine or chlorine); alkyl such as lower alkyl (e.g. methyl); alkoxy such as lower alkoxy (e.g. methoxy); haloalkyl such as halo lower alkyl (e.g. fluoroalkyl); halo lower alkylsulfinyl (e.g., —SOCF$_3$); or halo lower alkoxy (e.g., —OCHF$_2$). Presently preferred X, Y substituents are 2-F, 4-Cl; 2-F, 4-Br; 2,4-Cl$_2$; 2-Br, 4-Cl; and 2-F, 4-CF$_3$.

In each aspect of the invention it is often preferable that any alkyl, alkenyl, alkynyl or alkylene moiety (such as the hydrocarbon moiety of an alkoxy or haloalkoxy group) have up to about 6 carbon atoms, e.g., 1 to 4 or 5 carbon atoms, and that any cycloalkyl moiety have 3 to 7 ring carbon atoms, more preferably 3 to 6 carbon atoms.

Any acidic compound of this invention, including sulfonamides in which NR$^6$R$^7$ is NHSO$_2$R$^8$, may be converted to the corresponding base addition salt, such as a salt in which the salt-forming cation is Z (Z being as described above).

The present compounds may be prepared by methods described in the literature or in the following Examples or by methods analogous and similar thereto and within the skill of the art. In Example 3 below a compound of the formula

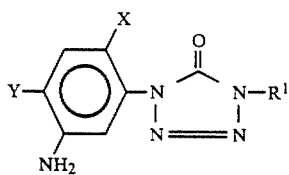

(such as the compound shown in Example 1E of International patent publication WO/03873, published July 2, 1987, in which X=F, Y=Cl and R$^1$=—(CH$_2$)$_3$F) is reacted (according to a procedure described by Doyle et al., J. Orq. Chem, 42, 2431 (1977)) with an alkyl nitrite, a copper (II) halide, and an olefinic compound having the formula CHR$^2$=CR$^4$Q' to form a compound of formula I above in which Q is —CH(R$^2$)C(R$^3$)(R$^4$)Q' and in which R$^3$ is halogen That compound may be dehydrohalogenated (e.g., with sodium hydride or other suitable base) to yield a compound of formula II above in which Q is —C(R$^2$)=C(R$^4$)Q'. To produce the latter, one may also use the method of Example 1 below starting with a compound of the formula

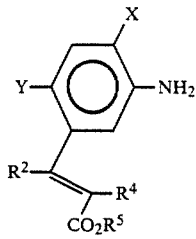

such as the 5-amino-2-chloro-4-fluorocinnamic acid ethyl ester described in Japanese published application 59-15538 of Sept. 4, 1984. The amino group is converted to a tetrazolinonyl group, as by a method described in the above-mentioned International patent publication WO 85/01939 (e.g., the method illustrated in Example 2 steps D and E thereof), forming a compound of the formula

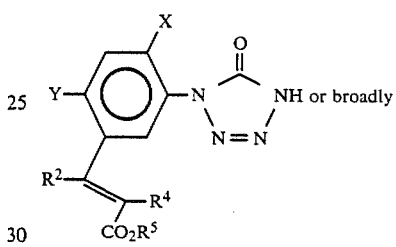

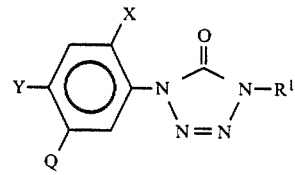

The R$^1$ substituent is then introduced, as by a method described in International patent publication WO 85/01939 (e.g., by reacting with a compound R-X' where X' is an appropriate leaving group such as halogen like Br, Cl or I, or alkylsulfonyloxy or aryl sulfonyloxy) to form a compound of the formula

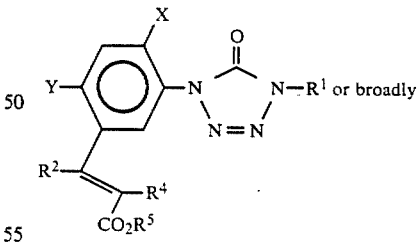

The —CH=C(R$^4$)CO$_2$R$^5$ group may be hydrogenated or halogenated to form a compound in which Q is —CH(R$^2$)C(R$^3$)(R$^4$)Q' and R$^2$ and R$^3$ are hydrogen (from hydrogenation as in Example 1D below) or R$^2$ and R$^3$ are halogen (from halogenation as in Example 2). When Q' is CO₂H, acidic compound of formula I may be converted to the corresponding amide, as by first treating with reagent such as thionyl chloride to form the acid halide (wherein Q' is, for example, —COCl) and then reacting with ammonia or an amine. Alternative methods of amide formation may involve known carbodiimide-mediated coupling.

As indicated above, the process involves the use of a reactant of the formula $CHR^2=CR^4Q'$. Among the reactants of this type which may be used are the following: methyl acrylate, ethyl acrylate, methyl methacrylate, methyl crotonate, methyl 3-chloroacrylate, methacrolein, vinylmethylketone, methacrylonitrile, and acrylamide.

The invention is illustrated further in the following Examples. In this application all parts are by weight and all temperatures are in °C. unless otherwise indicated.

EXAMPLE 1

Ethyl 3-[2-Chloro-4-fluoro-5-[4-(3-fluoropropyl)-1,4-dihydro-5-oxo-5H-tetrazol -1-yl]phenyl]propionate

STEP A Ethyl 3-[2-chloro-4-fluoro-5-(1,4-dihydro-5-oxo-5H-tetrazol-1-yl) phenyl]propenoate A stirred mixture of 8.06 g (0.0449 mole) of ethyl 3-(5-amino-2-chloro-4-fluorophenyl)propenoate and 5.32 g (0.0269 mole) of trichloromethyl chloroformate in 200 mL of 1,4-dioxane was heated at reflux for approximately three hours. The solvent was removed by distillation under reduced pressure, leaving a residue. To this residue was added 50 mL of trimethylsilyl azide, and the resultant mixture was stirred and heated at reflux for approximately 18 hours. The mixture was cooled and was diluted with toluene. The organic mixture was washed with water. The organic phase was evaporated under reduced pressure, leaving a residue. This residue was dissolved in ethyl acetate and was washed in succession with 1N hydrochloric acid, an aqueous, saturated sodium carbonate solution, and water. The washed organic phase was dried over anhydrous magnesium sulfate and was filtered. The filtrate was evaporated under reduced pressure leaving a residue. This residue was purified by column chromatography on silica gel to yield ethyl 3-[2-chloro-4-fluoro-5-(1,4-dihydro-5-oxo-5H-tetrazol-1-yl)phenyl]propenoate as a solid, mp 106°-109° C.

The ir and nmr spectra were consistent with the proposed structure.

STEP B 3-Fluoropropylmethane sulfonate

To an ice cold, stirred solution of 19.0 g (0.244 mole) of 3-fluoropropanol and 39.5 g (0.300 mole) of triethylamine in 300 mL of methylene chloride was added dropwise 34.4 g (0.300 mole) of methanesulfonyl chloride. The resultant mixture was allowed to warm to room temperature and was stirred for approximately 18 hours. The mixture was poured into water and was washed with an aqueous, saturated sodium bicarbonate solution. The organic phase was dried over anhydrous magnesium sulfate and was filtered. The filtrate was distilled under reduced pressure to yield 41.3 g of 3-fluoropropylmethane sulfonate as a liquid, bp 116° C./15 mm Hg.

The nmr spectrum was consistent with the proposed structure.

STEP C Ethyl 3-[2-chloro-4-fluoro-5-[4-(3-fluoropropyl) -1,4-dihydro-5-oxo-5H-tetrazol-1-yl]phenyl]propenoate To a stirred mixture of 2.62 g (0.00830 mole) of ethyl 3-[2-chloro-4-fluoro-5-(1,4-dihydro-5-oxo-5H-tetrazol-1-yl)phenyl]propenoate in 20 mL of N,N-dimethylformamide was added 1.46 g (0.00939 mole) of 3-fluoropropylmethane sulfonate and 1.30 g (0.00939 mole) of potassium carbonate. The reaction mixture was heated at 50°-60° C. and was stirred at that temperature for approximately 18 hours. The mixture was cooled and was poured into ice water. This mixture was extracted with ethyl acetate. The extract was dried over anhydrous magnesium sulfate and was filtered. The filtrate was evaporated under reduced pressure to yield 0.76 g of ethyl 3-[2-chloro-4-fluoro-5-[4-(3-fluoropropyl)-1,4-dihydro-5-oxo-5H-tetrazol -1yl]phenyl]propenoate as an oil, compound 4 of Table 1.

The nmr spectrum was consistent with the proposed structure.

Step D Ethyl 3-[2-chloro-4-fluoro-5-[4-(3-fluoropropyl) -1,4-dihydro-5-oxo-5H-tetrazol-1-yl]phenyl]propionate The hydrogenation of 0.45 g (0.0012 mole) of ethyl 3-[2-chloro-4-fluoro-5-[4-(3-fluoropropyl)-1,4-dihydro-5-oxo-5H-tetrazol -1-yl]phenyl]propenoate with approximately 0.1 g of platinum (IV) oxide in ethyl acetate yielded 0.43 g of ethyl 3-[2-chloro-4-fluoro-5-[4-(3-fluoropropyl) -1,4-dihydro-5-oxo-5H-tetrazol-1-yl]phenyl]propionate as an oil, compound 1 of Table 1.

The nmr and ir spectra were consistent with the proposed structure.

EXAMPLE 2

Ethyl 2,3-Dibromo-3-[2-chloro-4-fluoro-5-[4-(3-fluoropropyl) -1,4-dihydro-5-oxo-5H-tetrazol-1-yl]phenyl]propionate The bromination of 0.34 g (0.00091 mole) of ethyl 3-[2-chloro-4-fluoro -5-[4-(3-fluoropropyl)-1,4-dihydro-5-oxo-5H-tetrazol-1-yl]phenyl]propenoate with five drops of bromine in 10 mL of methylene chloride yielded 0.38 g of ethyl 2,3-dibromo-3-[2-chloro-4-fluoro-5-[4-(3-fluoropropyl) -1,4-dihydro-5-oxo-5H-tetrazol-1-yl]phenyl]propionate as an oil, compound 2 of Table 1.

The nmr and ir spectra were consistent with the proposed structure.

EXAMPLE 3

Ethyl 2-chloro-3-[2-chloro-4-fluoro-5-[4-(3-fluoropropyl) -1,4-dihydro-5-oxo-5H-tetrazol-1-yl]phenyl]propionate To an ice cold, stirred mixture of 5.54 g (0.0553 mole) of ethyl acrylate, 10 mL of acetonitrile, 0.43 g (0.0042 mole) of tert-butyl nitrite, and 0.45 g (0.0033 mole) of copper (II) chloride was added a solution of 0.80 g (0.0028 mole) of 1-(5-amino-4-chloro-2-fluorophenyl) -1,4-dihydro-4-(3-fluoropropyl)-5H-tetrazol-5-one (which may be prepared as described in International patent publication WO 87/03873, Example 1 A-E) in 10 mL of acetonitrile. The reaction mixture was stirred at room temperature for five hours and then was diluted with 2N hydrochloric acid. The acidic mixture was extracted with three portions of diethyl ether. The extracts were combined and dried over anhydrous magnesium sulfate. The dried organic phase was filtered and the filtrate was evaporated leaving a residue. This residue was purified by column chromatography on silica gel, eluting with n-heptane: ethyl acetate (2:1) to yield 1.1 g of ethyl 2-chloro-3-[2-chloro-4-fluoro-5-[4-(3-fluoropropyl)-1,4-dihydro-5-oxo-5H-tetrazol-1-yl]phenyl]propionate as an oil, compound 3 of Table 1.

The nmr spectrum was consistent with the proposed structure.

HERBICIDAL ACTIVITY

The plant test species used in demonstrating the herbicidal activity of compounds of this invention include cotton (*Gossvoium hirsutum* var. DPL61), soybean (*Glycine max* var. Williams), field corn (*Zea mays* var. Pioneer 3732), wheat (*Triticum aestivium* var. Wheaton), rice (*Oryza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence:

Two disposable fiber flats (8 cm×15 cm×25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |

| Herbicide Rating System | | | |
|---|---|---|---|
| Rating Percent Control | Description of Main Categories | Crop Description | Weed Description |
| 100 | Complete effect | Complete crop destruction | Complete weed destruction |

Herbicidal data at selected application rates are given for various compounds of the invention in Tables 2 and 3 below. The test compounds are identified in the tables by numbers which correspond to those in Table 1. The abbreviation "kg/ha" in Tables 2 and 3 means kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequency from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surfaceactive agents are available in commerce. The surfaceactive agent, when used, normally comprises from 1 to 15% by weight of the composition.

Other useful formulations include simple solutions or suspensions of the active ingredient in a relatively nonvolatile solvent such as water, corn oil, kerosene, propylene glycol, or other suitable solvents. The following illustrate specific suspensions:

| Oil Suspension: | % by Wt. |
|---|---|
| Active ingredient | 25.00 |
| Polyoxyethylene sorbitol hexaoleate | 5.00 |
| Highly aliphatic hydrocarbon oil | 70.00 |
| Total | 100.00 |

| Aqueous Suspension: | % by Wt. |
|---|---|
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or waterdispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; for example, with Compound 3 (Table 1) applied postemergently, an amount in the range of about 15 to 125 g/ha, such as about 30 to 60 g/ha, may be employed for control of broad leaf weeds with tolerance for crops such as wheat and maize. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl) acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl) benzeneamine (trifluralin); aryl urea herbicides such as N'-(3,4-dichlorophenyl)-N,N-dimethylurea (diuron) and N,N-dimethyl-N'-[3-(trifluoromethyl) phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

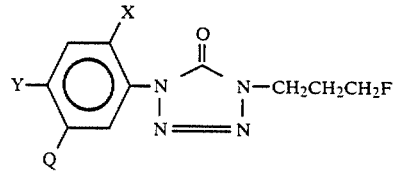

| Cmpd No. | X | Y | Q |
|---|---|---|---|
| 1 | F | Cl | $CH_2CH_2CO_2C_2H_5$ |
| 2 | F | Cl | $CH(Br)CH(Br)CO_2C_2H_5$ |
| 3 | F | Cl | $CH_2CH(Cl)CO_2C_2H_5$ |
| 4 | F | Cl | $CH=CHCO_2C_2H_5$ |
| 5 | Cl | Cl | $CH_2CH_2CO_2CH_3$ |
| 6 | Cl | Cl | $CH_2CH(Cl)CO_2H$ |
| 7 | Cl | Cl | $CH_2CH(Cl)CO_2CH_3$ |
| 8 | Cl | Cl | $CH_2CH(Cl)CO_2C_2H_5$ |
| 9 | Cl | Cl | $CH_2CH(Br)CO_2C_2H_5$ |
| 10 | Cl | Cl | $CH_2CH(Cl)CO_2CH(CH_3)_2$ |
| 11 | Cl | Cl | $CH_2CH(Cl)CO_2CH(CH_3)CH_2CH_3$ |

TABLE 1-continued

Structure: Phenyl ring with X, Y, Q substituents; N-N=N tetrazole ring with C(=O)-N-CH₂CH₂CH₂F

| Cmpd No. | X | Y | Q |
|---|---|---|---|
| 12 | Cl | Cl | CH₂CH(Cl)CO₂CH₂C₆H₅ |
| 13 | Cl | Cl | CH(Br)CH(Br)CO₂CH₃ |
| 14 | Cl | Cl | CH(Br)CH(Br)CO₂C₂H₅ |
| 15 | Cl | Cl | CH(CH₃)CH(Cl)CO₂C₂H₅ |
| 16 | F | Cl | CH₂C(Cl)(CH₃)CO₂CH₃ |
| 17 | Cl | Cl | CH₂CH(Cl)C(O)NH₂ |
| 18 | Cl | Cl | CH₂CH(Cl)C(O)NHCH₃ |
| 19 | Cl | Cl | CH₂CH(Cl)C(O)N(CH₃)₂ |
| 20 | Cl | Cl | CH₂CH(Cl)C(O)NH-cyclopropyl |
| 21 | Cl | Cl | CH₂CH(Cl)C(O)NHCH₂CH=CH₂ |
| 22 | Cl | Cl | CH₂CH(Cl)C(O)NHCH₂CN |
| 23 | Cl | Cl | CH₂CH(Cl)C(O)NHOH |
| 24 | Cl | Cl | CH₂CH(Cl)C(O)NHOCH₃ |
| 25 | Cl | Cl | CH₂CH(Cl)C(O)N(CH₃)OCH₃ |
| 26 | Cl | Cl | CH₂CH(Cl)C(O)NHC₆H₄-4-Cl |
| 27 | Cl | Cl | CH₂CH(Cl)C(O)NHCH₂C₆H₄-4-Cl |
| 28 | Cl | Cl | CH₂CH(Cl)C(O)NHSO₂CH₃ |
| 29 | Cl | Cl | CH₂CH(Cl)C(O)NHSO₂C₆H₄-4-Cl |
| 30 | Cl | Cl | CH₂CH(Cl)C(O)NHSO₂C₆H₄-4-CH₃ |
| 31 | F | Cl | CH₂CH(CH₃)CO₂CH₃ |
| 32 | F | Cl | CH₂CH(Cl)C(O)NH-cyclopropyl |
| 33 | F | Cl | CH₂CH(Cl)C(O)NHCH₂CN |
| 34 | F | Cl | CH₂CH(Cl)C(O)N(CH₃)OCH₃ |
| 35 | F | Cl | CH₂CH(Cl)C(O)NHSO₂CH₃ |
| 36 | F | Cl | CH₂CH(Cl)C(O)NHSO₂CF₃ |
| 37 | F | Cl | CH₂CH(Cl)C(O)NHSO₂C₆H₄-2-Cl |
| 38 | F | Cl | CH₂CH(Cl)C(O)NHSO₂C₆H₄-3-Cl |
| 39 | F | Cl | CH₂CH(Cl)C(O)NHSO₂C₆H₄-4-Cl |
| 40 | F | Cl | CH₂CH(Cl)C(O)NHSO₂CH(CH₃)₂ |
| 41 | F | Cl | CH₂CH(Cl)C(O)NHSO₂C₆H₄-4-CH₃ |
| 42 | Cl | Cl | CH=CHCO₂CH₃ |
| 43 | Cl | Cl | CH=CHCO₂C₂H₅ |
| 44 | Cl | Cl | CH=CHCO₂CH₂C₆H₅ |
| 45 | F | Cl | CH=C(CH₃)CO₂CH₃ |
| 46 | Cl | Cl | CH₂CH(Cl)CN |
| 47 | F | Cl | CH₂CH(Cl)CO₂CH₃ |
| 48 | F | Cl | CH₂CH(Cl)COOH |
| 49 | Cl | Cl | CH₂CH(Cl)COCH₃ |
| 50 | Cl | Cl | CH₂CH(Cl)CONHCH₂CH₂CH₃ |
| 51 | Cl | Cl | CH₂CH(Cl)CONHCH₂CH₂CH₂CH₃ |
| 52 | Cl | Cl | CH₂CH(Cl)CONHCH(CH₃)CH₂CH₃ |
| 53 | Cl | Cl | CH₂CH(Cl)CONH-cyclopentyl |
| 54 | Cl | Cl | CH=CHCONH-cyclopentyl |
| 55 | Cl | Cl | CH=CHCONHCH₂CH₂CH₃ |
| 56 | Cl | Cl | CH=CHCONHCH(CH₃)CH₂CH₃ |
| 57 | F | Cl | CH=CHCO₂CH₃ |
| 58 | F | Cl | CH₂CH(Cl)CO₂CH(CH₃)₂ |
| 59 | Cl | Cl | CH₂CH(Cl)CONHCH(CH₃)₂ |
| 60 | Cl | Cl | CH=CHCONHCH(CH₃)₂ |
| 61 | Cl | Cl | CH₂CH(Cl)CONHC₂H₅ |
| 62 | Cl | Cl | CH=CHCONHC₂H₅ |
| 63 | F | Cl | CH₂CH(Cl)CHO |
| 64 | F | Cl | CH₂CH(Cl)CO⁻₂ ⁺K |
| 65 | F | Cl | CH₂CH(Cl)CO⁻₂NH⁺(C₂H₅)₃ |
| 66 | Cl | Cl | CH₂CH(Cl)CO⁻₂Na⁺ |
| 67 | Cl | Cl | CH₂CH(Cl)CO⁻₂NH⁺(C₂H₅)₃ |

TABLE 2

Preemergence Herbicidal Activity
% Control @ 0.5 kg/ha

| Cmpd. No. Species | 1 | 2 | 3 | 4 |
|---|---|---|---|---|
| Cotton | 30 | 20 | 95 | 40 |
| Soybean | 5 | 5 | 0 | 10 |
| Corn | 5 | 10 | 5 | 5 |
| Rice | 30 | 5 | 20 | 20 |
| Wheat | 5 | 5 | 15 | 30 |
| Morningglory | 10 | 80 | 100 | 80 |
| Wild Mustard | 100 | 100 | 100 | 100 |
| Velvetleaf | 100 | 100 | 100 | 100 |
| Barnyardgrass | 80 | 40 | 20 | 80 |
| Green Foxtail | 70 | 0 | 60 | 70 |
| Johnsongrass | 90 | 5 | 70 | 70 |

TABLE 3

Postemergence Herbicidal Activity
% Control @ 0.5 kg/ha

| Cmpd. No. Species | 1 | 2 | 3 | 4 |
|---|---|---|---|---|
| Cotton | 100 | 90 | 100 | 100 |
| Soybean | 70 | 60 | 90 | 75 |
| Corn | 60 | 50 | 30 | 70 |
| Rice | 40 | 15 | 50 | 30 |
| Wheat | 30 | 40 | 95 | 70 |
| Morningglory | 85 | 95 | 100 | 90 |
| Wild Mustard | 100 | 100 | 100 | 100 |
| Velvetleaf | 100 | 100 | 100 | 100 |
| Barnyardgrass | 50 | 10 | 15 | 50 |
| Green Foxtail | 60 | 30 | 15 | 90 |
| Johnsongrass | 90 | — | 95 | 80 |

I claim:

1. A herbicidal compound which is a Q-substituted 1-phenyl-4-substituted-1,4-dihydro-5H-tetrazol-5-one in which the Q-substituent is bonded to the ring-carbon atom at the 5-position of the phenyl group and in which:

Q is —CH($R^2$)C($R^3$)($R^4$)Q' or —C($R^2$)=C($R^4$)Q';

$R^2$ and $R^3$ are each, independently, hydrogen, alkyl, or halogen; and $R^4$ is hydrogen or lower alkyl;

said compound being: (a) a carboxylic acid in which Q' is COOH or (b) a salt, ester, amide, or nitrile of said carboxylic acid, said compound being one whose 5-methoxy analog and 5-propargyloxy analog are herbicides.

2. A herbicidal compound which is a Q-substituted 1-phenyl-4-substituted-1,4-dihydro-5H-tetrazol-5 one in which the Q-substituted is bonded to the ring-carbon atom at the 5-position of the phenyl group and in which:

Q is —CH($R^2$)C($R^3$)($R^4$)Q' or —C($R^2$)=C($R^4$)Q';

$R^2$ and $R^3$ are each, independently, hydrogen, halogen or alkyl;

$R^4$ is hydrogen or lower alkyl;

Q' is COOH, COOZ, COOR⁵, CON($R^6$)($R^7$), CN, CHO or C(O)$R^5$;

Z is a salt-forming cation;

R5 is alkyl, cycloalkyl or aralkyl;

each of $R^6$ and $R^7$ is, independently, hydrogen, alkyl, cycloalkyl, alkenyl, alkynyl, alkoxy, phenyl, benzyl, or SO₂$R^8$ or is one of said radicals substituted by halogen, alkyl, or cyano; $R^8$ being the same as $R^6$ other than hydrogen or SO₂$R^6$; said compound being one whose 5-methoxy analog and 5-propargyloxy analog are herbicides.

3. A compound as in claim 2, having the formula

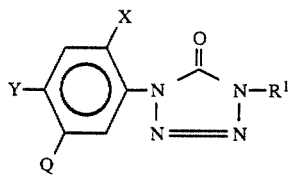

in which R[1] is lower alkyl or haloalkyl; X is hydrogen, halogen, alkyl, haloalkyl, alkoxy, or nitro; and Y is hydrogen, halogen, alkyl, alkoxy, haloalkyl, halo lower alkylsulfinyl, or halo lower alkoxy.

4. A compound as in claim 3 in which R[1] is $CH_2CH_2CH_2F$, X is F or Cl, and Y is Cl or Br.

5. A compound as in claim 4 in which Q is $CH_2CH(Cl)Q'$.

6. A compound as in claim 5 in which Q' is $CO_2R^5$ and R[5] is lower alkyl.

7. A compound as in claim 6 in which R[5] is ethyl.

8. A compound as in claim 3 in which Q is $CH=CHQ'$.

9. A compound as in claim 3 in which Q is $CH_2CH_2Q'$.

10. A compound as in claim 3 in which Q is $CH_2CH(Cl)Q'$.

11. A compound as in claim 4 in which Q is $CH=CHQ'$.

12. A compound as in claim 4 in which Q is $CH_2CH_2Q'$.

13. A herbicidal composition comprising a herbicidally effective amount of the compound of claim 1 in admixture with a suitable carrier.

14. A method for controlling undesired plant growth which comprises applying to the locus where control is desired a herbicidally effective amount of the composition of claim 13.

15. A herbicidal composition comprising a herbicidally effective amount of the compound of claim 2 in admixture with a suitable carrier.

16. A method for controlling undesired plant growth which comprises applying to the locus where control is desired a herbicidally effective amount of the composition of claim 15.

17. A herbicidal composition comprising a herbicidally effective amount of the compound of claim 3 in admixture with a suitable carrier.

18. A method for controlling undesired plant growth which comprises applying to the locus where control is desired a herbicidally effective amount of the composition of claim 17.

19. A herbicidal composition comprising a herbicidally effective amount of the compound of claim 4 in admixture with a suitable carrier.

20. A method for controlling undesired plant growth which comprises applying to the locus where control is desired a herbicidally effective amount of the composition of claim 19.

21. A herbicidal composition comprising an herbicidally effective amount of the compound of claim 5 in admixture with a suitable carrier.

22. A method for controlling undesired plant growth which comprises applying to the locus where control is desired a herbicidally effective amount of the composition of claim 21.

23. A herbicidal composition comprising an herbicidally effective amount of the compound of claim 6 in admixture with a suitable carrier.

24. A method for controlling undesired plant growth which comprises applying to the locus where control is desired a herbicidally effective amount of the composition of claim 23.

25. A herbicidal composition comprising a herbicidally effective amount of the compound of claim 7 in admixture with a suitable carrier.

26. A method for controlling undesired plant growth which comprises applying to the locus where control is desired a herbicidally effective amount of the composition of claim 25.

27. A herbicidal composition comprising a herbicidally effective amount of the compound of claim 8 in admixture with a suitable carrier.

28. A method for controlling undesired plant growth which comprises applying to the locus where control is desired a herbicidally effective amount of the composition of claim 27.

29. A herbicidal composition comprising an herbicidally effective amount of the compound of claim 9 in admixture with a suitable carrier.

30. A method for controlling undesired plant growth which comprises applying to the locus where control is desired a herbicidally effective amount of the composition of claim 29.

31. A herbicidal composition comprising an herbicidally effective amount of the compound of claim 10 in admixture with a suitable carrier.

32. A method for controlling undesired plant growth which comprises applying to the locus where control is desired a herbicidally effective amount of the composition of claim 31.

33. A herbicidal composition comprising a herbicidally effective amount of the compound of claim 11 in admixture with a suitable carrier.

34. A method for controlling undesired plant growth which comprises applying to the locus where control is desired a herbicidally effective amount of the composition of claim 33.

35. A herbicidal composition comprising a herbicidally effective amount of the compound of claim 12 in admixture with a suitable carrier.

36. A method for controlling undesired plant growth which comprises applying to the locus where control is desired a herbicidally effective amount of the composition of claim 35.

* * * * *